US00PP25013P3

(12) United States Plant Patent
Blom

(10) Patent No.: US PP25,013 P3
(45) Date of Patent: Oct. 28, 2014

(54) ***CHRYSANTHEMUM* PLANT NAMED 'ZANMURADIANT'**

(50) Latin Name: ***Chrysanthemum×morifolium* Ramat.**
Varietal Denomination: Zanmuradiant

(71) Applicant: Chrysanthemum Breeders Association Research B.V., Aalsmeer (NL)

(72) Inventor: Wilhelmus Bernardus Blom, Leimuiden (NL)

(73) Assignee: Chrysanthemum Breeders Association Research B.V., Valkenburg (NL)

( * ) Notice: Subject to any disclaimer, the term of this patent is extended or adjusted under 35 U.S.C. 154(b) by 0 days.

(21) Appl. No.: 13/694,700

(22) Filed: Dec. 26, 2012

(65) Prior Publication Data
US 2014/0182033 P1 Jun. 26, 2014

(51) Int. Cl.
*A01H 5/00* (2006.01)

(52) U.S. Cl.
USPC ..... Plt./287

(58) Field of Classification Search
USPC ..... Plt./287, 293
See application file for complete search history.

*Primary Examiner* — Anne Grunberg
(74) *Attorney, Agent, or Firm* — Steptoe & Johnson LLP

(57) ABSTRACT

A *Chrysanthemum* plant named 'Zanmuradiant' characterized by its large sized blooms with red-purple ray florets and prolific branching; natural season flowering date September 12 (week 37); blooming for a period of 4 weeks.

3 Drawing Sheets

Botanical designation: *Chrysanthemum×morifolium* Ramat.

Cultivar denomination: 'Zanmuradiant'.

BACKGROUND OF THE INVENTION

The present invention relates to a new and distinct cultivar of *Chrysanthemum* plant, botanically known as *Chrysanthemum×morifolium* Ramat., commercially known as a garden mum, and hereinafter referred to by the cultivar denomination 'Zanmuradiant'. 'Zanmuradiant' is a product of a breeding and selection program for outdoor pot mums (garden mums) which had the objective of creating new cultivars with a double type inflorescence, a natural season flowering date around September 12 (week 37), blooming for a period of 4 weeks. 'Zanmuradiant' is a seedling resulting from a cross of unregistered parent plants.

The new and distinct cultivar was discovered and selected as a flowering plant by Wilhelmus Bernardus Blom on a cultivated field in Rijsenhout, The Netherlands in 2008. The first act of asexual production of 'Zanmuradiant' was accomplished when vegetative cuttings from the initial selection in 2008 were propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct variety of *Chrysanthemum* (of about 16 weeks) is shown in the accompanying drawings, the color being as nearly true as possible with color photographs of this type.

DESCRIPTION OF THE INVENTION

Figure 1:
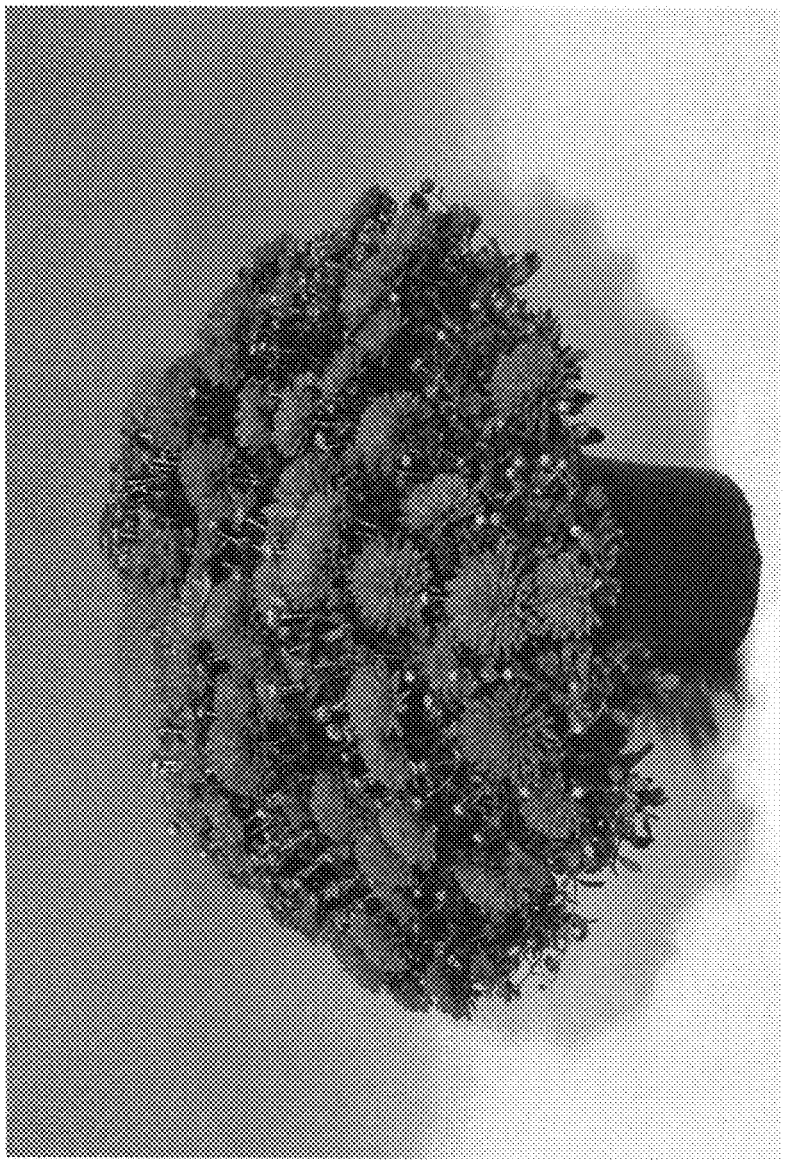
FIG. 1 shows a plant of the cultivar in full bloom.
Figure 2:
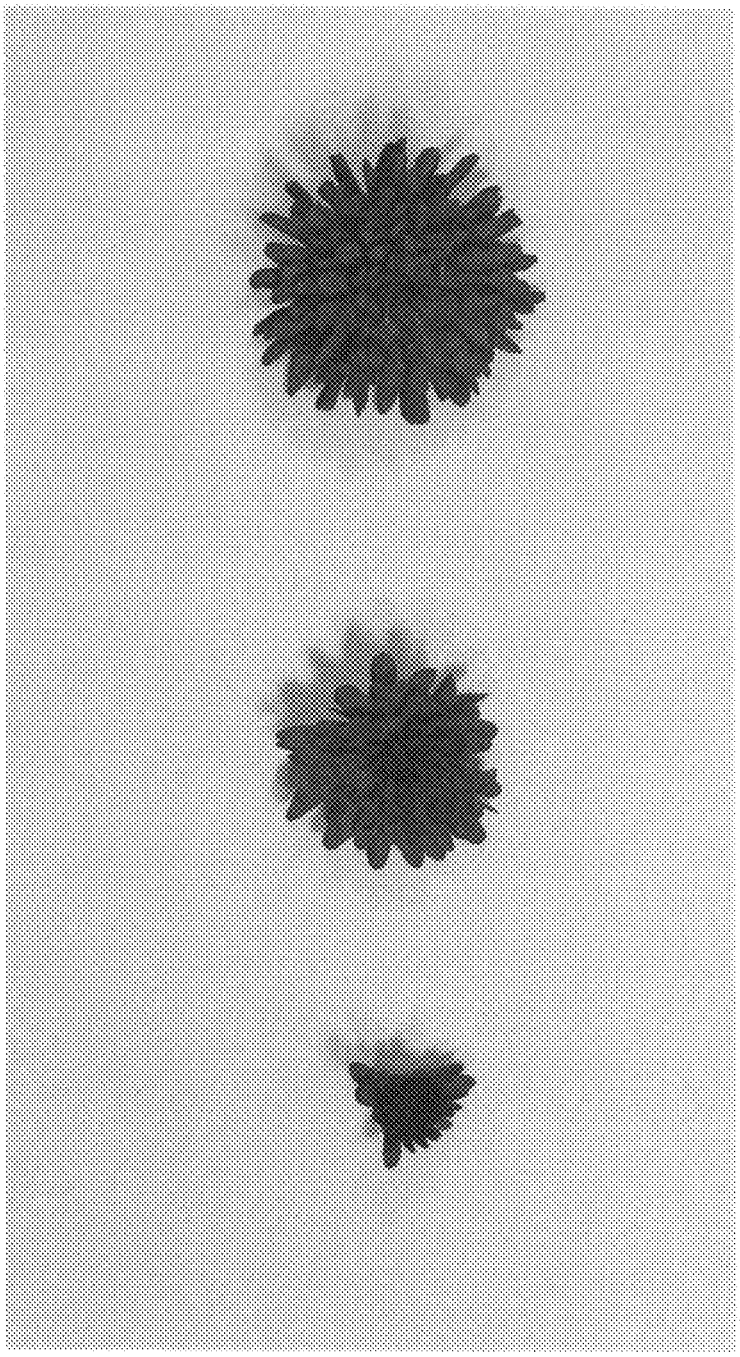
FIG. 2 shows the various stages of bloom of the new cultivar.
Figure 3:
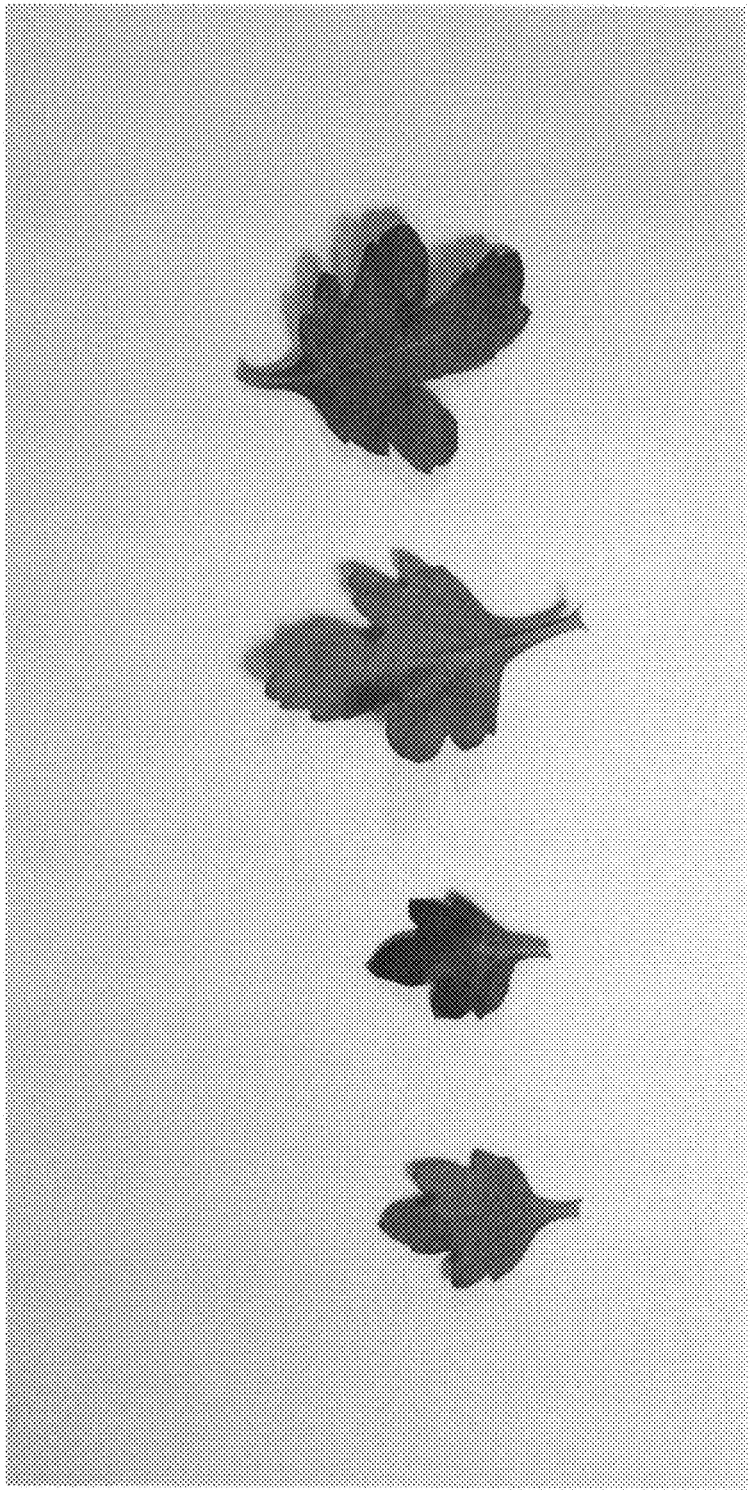
FIG. 3 shows the various stages of foliage of the new cultivar.

The observations and measurements were gathered from plants grown out door in Rijsenhout, The Netherlands under natural day length and temperature and planted in week 22 in 2011. The natural blooming date of this crop was September 12 (week 37). The average height of the plants was 30 cm. No growth retardants were used. No tests were done on disease or insect resistance or susceptibility. No tests were done on cold or drought tolerance. This new variety produces large sized blooms with red-purple ray florets blooming for a period of 4 weeks.

From the cultivars known to inventor the most similar existing cultivar in comparison to 'Zanmuradiant' is 'Manakin' (U.S. Plant Pat. No. 11,521). When 'Manakin' and 'Zanmuradiant' are being compared the following difference is noticed: The differences of 'Manakin' and 'Zanmuradiant' are (1) Bloom size. And (2) Color ray-florets. (1) The blooms of 'Manakin' are smaller than those of 'Zanmuradiant'. (2) The ray-florets of 'Manakin' are less purple than those of 'Zanmuradiant'

The following is a description of the plant and characteristics that distinguish 'Zanmuradiant' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

Botanical Description of *Chrysanthemum* ×*morifolium* Ramat. 'Zanmuradiant'

| | |
|---|---|
| **Bud** | |
| Size: | Small; cross-section 5 mm, height 5 mm |
| Shape: | Round |
| Texture: | Pubescent |
| Outside color: | Greyed-green 191A |
| **Phyllaries** | |
| Number: | 25, arranged in 3 rows |
| Shape: | Elliptic |
| Apex: | Acute |
| Base: | Truncate |
| Margin: | Entire |
| Color: | Upper side: Green N138B<br>Lower side: Green 139B |
| Length and width: | 5 mm; 2.5 mm |
| Texture: | Pubescent |
| **Inflorescences** | |
| Type: | Double |
| Height: | 2.5 cm |
| Diameter: | 5.5-6 cm |
| Peduncle length: | 5-8 cm |
| Peduncle color: | Green 138B |
| Peduncle diameter: | 1.5 mm |
| Peduncle texture: | Pubescent |
| Number per branch: | Approx. 8-10 inflorescences |
| Duration of flowering: | 4 weeks |
| Seeds: | Produced in small quantities, ovate, Greyed-brown 199A, length 1.5 mm, diameter 0.5 mm |
| Fragrance: | Faint *chrysanthemum* odor |
| **Color inflorescences** | |
| Center of inflorescence: | Immature stage: Red-purple 59A;<br>Mature stage: Red-purple 59A |
| Color of upper side of ray florets: | Red-purple 59B |
| Color of lower side of ray florets: | Greyed-red 178C |
| Tonality from distance: | A garden mum with red purple blooms |
| Color of ray florets after aging of the plant: | Greyed-purple 187A |
| **Ray florets** | |
| Texture: | Upper and lower side smooth |
| Number: | 220-230 |
| Shape: | Elliptic |
| Apex: | Dentate |
| Base: | Attenuate |
| Cross-section: | Flat |
| Longitudinal axis: | Straight |
| Length of corolla tube: | 4-5 mm |
| Ray floret margin: | Entire |
| Ray floret length: | 1.6-2.8 cm |
| Ray floret width: | 4 mm |
| Ratio length/width: | High |
| Disc florets | Absent |
| **Receptacle** | |
| Color: | Yellow-green 145D |
| Shape: | Conical raised |
| Height: | 5 mm |
| Diameter: | 5 mm |
| **Reproductive Organs** | |
| Androecium: | Absent |
| Gynoecium: | Present in ray florets |
| Style color: | Yellow-green 154C |
| Style length: | 3 mm |

TABLE 1-continued

Botanical Description of *Chrysanthemum* ×*morifolium* Ramat. 'Zanmuradiant'

| | |
|---|---|
| Stigma color: | Yellow 7A |
| Stigma width: | 1 mm |
| Ovary: | Enclosed in calyx |
| **Plant** | |
| Form: | Grown as a spray type pot mum, outdoor raised and mounded |
| Growth habit: | Spherical shape |
| Growth rate: | Medium to high |
| Height: | 30 cm |
| Width: | 45-50 cm |
| Stem color: | Greyed-brown 199A |
| Stem strength: | Not strong |
| Stem brittleness: | Brittle |
| Stem anthocyanin coloration: | streaks of Greyed-purple 187C |
| Internode length: | 1.5-2.5 cm |
| Length of lateral branch: | From top to bottom 18-20 cm |
| Lateral branch color: | Green 137 C |
| Lateral branch, attachment: | Brittle |
| Lateral branch diameter: | 3 mm |
| Branching (average number of lateral branches): | Prolific with 7-9 breaks after pinching |
| Natural season blooming date: | September 12 (week 37-40) |
| **Foliage** | |
| Leaf color: | Upper side: Green 137A;<br>Lower side: Green 138A |
| Color midvein: | Upper side: Yellow-green 147D;<br>Lower side: Yellow-green 148D |
| Size: | Small; length 3-5 cm, width 2-3.5 cm |
| Quantity (number per lateral branches): | 14-16 |
| Shape: | Broadly elliptic |
| Texture upper side: | Sparsely pubescent |
| Texture under side: | Pubescent |
| Venation arrangement: | Palmate |
| Shape of margin: | Serrated |
| Shape of base of sinus between lateral lobes: | Rounded |
| Margin of sinus between lateral lobes: | Diverging |
| Shape of base: | Attenuate to truncate |
| Apex: | Mucronulate |
| Petiole length: | 0.2-0.5 cm |
| Petiole diameter: | 1-1.5 mm |
| Petiole color: | Yellow-green 147D |

TABLE 2

Differences with the comparison variety (when grown under identical conditions).

| | 'Zanmuradiant' | 'Manakin' |
|---|---|---|
| Inflorescence diameter | 5.5-6 cm | 3.5 cm |
| Color upper surface ray-florets | Red-purple 59B | Red 46A |

I claim:

1. A new and distinct *Chrysanthemum* plant named 'Zanmuradiant' as described and illustrated.

* * * * *